United States Patent
Schmidt et al.

(10) Patent No.: US 12,024,425 B2
(45) Date of Patent: Jul. 2, 2024

(54) METHOD FOR PREPARING AN IMIDE SALT CONTAINING A FLUOROSULPHONYL GROUP

(71) Applicant: Arkema France, Colombes (FR)

(72) Inventors: Grégory Schmidt, Pierre-Benite (FR); Jérémy Bauche, Pierre-Benite (FR); Dominique Deur-Bert, Pierre-Benite (FR)

(73) Assignee: ARKEMA FRANCE, Colombes (FR)

( * ) Notice: Subject to any disclaimer, the term of this patent is extended or adjusted under 35 U.S.C. 154(b) by 851 days.

(21) Appl. No.: 17/056,441

(22) PCT Filed: May 21, 2019

(86) PCT No.: PCT/FR2019/051149
§ 371 (c)(1),
(2) Date: Nov. 18, 2020

(87) PCT Pub. No.: WO2019/224471
PCT Pub. Date: Nov. 28, 2019

(65) Prior Publication Data
US 2021/0206637 A1  Jul. 8, 2021

(30) Foreign Application Priority Data
May 23, 2018 (FR) ...................................... 1854314

(51) Int. Cl.
*C01B 21/086* (2006.01)
*C07F 1/02* (2006.01)
*H01M 10/0525* (2010.01)
*H01M 10/0568* (2010.01)

(52) U.S. Cl.
CPC .............. *C01B 21/086* (2013.01); *C07F 1/02* (2013.01); *H01M 10/0525* (2013.01); *H01M 10/0568* (2013.01)

(58) Field of Classification Search
CPC ....... C01B 21/086; C01B 21/093; C07F 1/02; H01M 10/0525; H01M 10/0568; H01M 10/052; Y02E 60/10; C07C 303/40
See application file for complete search history.

(56) References Cited

U.S. PATENT DOCUMENTS

| 9,650,250 | B2 | 5/2017 | Maruyama | |
| 10,128,525 | B2 * | 11/2018 | Schmidt | H01M 10/058 |
| 2014/0075746 | A1 | 3/2014 | Schmidt | |
| 2015/0175422 | A1 | 6/2015 | Maruyama | |
| 2015/0246812 | A1 | 9/2015 | Audureau et al. | |
| 2017/0047607 | A1 * | 2/2017 | Schmidt | C01B 21/086 |
| 2021/0122634 | A1 | 4/2021 | Leduc et al. | |
| 2021/0214220 | A1 | 7/2021 | Schmidt et al. | |

FOREIGN PATENT DOCUMENTS

| CN | 106006586 | A | 10/2016 | |
| EP | 2881365 | A1 | 6/2015 | |
| WO | 2012160280 | A2 | 11/2012 | |
| WO | 2014080120 | A1 | 5/2014 | |
| WO | 2015158979 | A1 | 10/2015 | |
| WO | WO-2018072024 | A1 * | 4/2018 | ........... C01B 21/096 |

OTHER PUBLICATIONS

International Search Report (PCT/ISA/210) issued on Sep. 9, 2019, by the European Patent Office as the International Searching Authority for International Application No. PCT/FR2019/051149.
Written Opinion (PCT/ISA/237) issued on Sep. 9, 2019, by the European Patent Office as the International Searching Authority for International Application No. PCT/FR2019/051149.
U.S. Appl. No. 17/056,781, Leduc et al.
Written Opinion (PCT/ISA/237) and International Search Report (PCT/ISA/210) mailed on Aug. 2, 2019, by the European Patent Office as the International Searching Authority for International Application No. PCT/FR2019/051148, European Patent Office, Rijswijk, NL, 9 pages.
Beran, M., et al., "A New Method of the Preparation of Imido-bis(sulfuric acid) Dihalogenide, (F,Cl), and the Potassium Salt of Imido-bis(sulfuric acid) Difluoride", Z. Anorg. Allg. Chem., 2005, pp. 55-59, vol. 631, Wiley-VCH Verlag Gmbh & Co. KGaA, Weinheim, DE, (XP002788725).
Lehner, M., et al., "Separation of Dust, Halogen and PCDD/F in a Compact Wet Scrubber", Trans Icheme, Mar. 2001, pp. 109-116, vol. 79B, Institution of Chemical Engineers (XP002788727).
Roy, P., et al., "Emission Control and Finding a Way Out to Produce Sulphuric Acid from Industrial SO2 Emission", J Chem Eng Process Technol, 2015, 7 pages, vol. 6, No. 2, 230 (XP002788726).
Leduc, Philippe, et al., U.S. Appl. No. 17/056,781 entitled "Method for Preparing Lithium Bis(Fluorosulphonyl) Imide Salt," filed in the U.S. Patent and Trademark Office Nov. 19, 2020.

* cited by examiner

*Primary Examiner* — Daniel Berns
*Assistant Examiner* — Syed T Iqbal
(74) *Attorney, Agent, or Firm* — BUCHANAN, INGERSOLL & ROONEY PC

(57) ABSTRACT

A method for preparing a compound having the following formula (IV): $R_2$—$(SO_2)$—NLi—$(SO_2)$—F (IV), the method including a step a) of reacting a sulphamide having the following formula (A): $R_0$—$(SO_2)$—$NH_2$ (A) with at least one sulphur-containing acid and at least one chlorinating agent, the step a) being carried out: at a temperature between 90° C. and 130° C., and at a pressure which is strictly greater than 7 bar (absolute).

16 Claims, No Drawings

METHOD FOR PREPARING AN IMIDE SALT CONTAINING A FLUOROSULPHONYL GROUP

FIELD OF THE INVENTION

The present invention relates to a process for preparing imide salts containing a fluorosulfonyl group.

TECHNICAL BACKGROUND

By virtue of their very low basicity, anions of sulfonylimide type are increasingly used in the field of energy storage in the form of inorganic salts in batteries, or of organic salts in supercapacitors or in the field of ionic liquids. Since the battery market is booming and the reduction of battery manufacturing costs is becoming a major issue, a large-scale, low-cost synthesis process for anions of this type is required.

In the specific field of Li-ion batteries, the salt currently most widely used is $LiPF_6$, but this salt exhibits many disadvantages, such as a limited thermal stability, a sensitivity to hydrolysis and therefore a lower battery safety. Recently, new salts bearing the $FSO_2-$ group have been studied and have demonstrated many advantages, such as better ion conductivity and resistance to hydrolysis. One of these salts, LiFSI ($LiN(FSO_2)_2$), has shown highly advantageous properties which make it a good candidate for replacing $LiPF_6$.

WO 2015/158979 describes in particular the preparation of LiFSI via a step of chlorinating sulfamic acid, with thionyl chloride and sulfuric acid, at atmospheric pressure (examples). However, after 24 hours at reflux of the thionyl chloride, the conversion of the sulfamic acid is not complete.

There is therefore a need for a process for preparing an imide salt comprising a fluorosulfonyl group which does not have the abovementioned drawbacks. In particular, there is a need for a process allowing a (quasi)-total conversion of the sulfamide reagent in a reduced time.

DESCRIPTION OF THE INVENTION

The present invention relates to a process for preparing a compound of the following formula (IV):

$$R_2-(SO_2)-NLi-(SO_2)-F \quad (IV)$$

wherein $R_2$ represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$;
$R_2$ preferably representing F;
said process comprising a step a) of reacting a sulfamide of the following formula (A):

$$R_0-(SO_2)-NH_2 \quad (A)$$

wherein $R_0$ represents one of the following radicals: OH, Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$;
with at least one sulfur-containing acid and at least one chlorinating agent, said step a) being carried out:
at a temperature between 90° C. and 130° C., preferably between 100° C. and 130° C.; and
at a pressure strictly greater than 7 bar abs.
Step a) advantageously results in a compound of formula (I):

$$R_1-(SO_2)-NH-(SO_2)-Cl \quad (I)$$

wherein $R_1$ represents one of the following radicals: Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$; $R_1$ preferably representing Cl.

Preferably, the compound (A) is that wherein $R_0$ represents OH.

According to the invention, the sulfur-containing agent can be chosen from the group consisting of chlorosulfonic acid ($ClSO_3H$), sulfuric acid, oleum, and mixtures thereof.

Preferably, the sulfur-containing agent is sulfuric acid or oleum, preferably sulfuric acid.

According to the invention, the chlorinating agent can be chosen from the group consisting of thionyl chloride ($SOCl_2$), oxalyl chloride ($COCl_2$), phosphorus pentachloride ($PCl_5$), phosphonyl trichloride ($PCl_3$), phosphoryl trichloride ($POCl_3$), and mixtures thereof.

Preferably, the chlorinating agent is thionyl chloride.

Step a) can be carried out in the presence of a catalyst, such as, for example, chosen from a tertiary amine (such as trimethylamine, triethylamine or diethylmethylamine); pyridine; and 2,6-lutidine.

Preferably, the reaction is performed in the absence of catalyst.

The molar ratio between the sulfur-containing acid and the compound (A) (in particular wherein $R_0=OH$) can be between 0.7 and 5, preferably between 0.9 and 5.

The molar ratio between the chlorinating agent and the compound (A) (in particular wherein $R_0=OH$) can be between 2 and 10, preferably between 2 and 5.

In particular, when the sulfur-containing agent is chlorosulfonic acid, the molar ratio between the latter and the compound (A) (in particular wherein $R_0=OH$) is between 0.9 and 5, and/or the molar ratio between the chlorinating agent and the compound (A), in particular with $R_0=OH$, is between 2 and 5.

In particular, when the sulfur-containing agent is sulfuric acid (or oleum), the molar ratio between the sulfuric acid (or oleum) and the compound (A) (in particular wherein $R_0=OH$), is between 0.7 and 5.

In particular, when the sulfur-containing agent is sulfuric acid (or oleum), the molar ratio between the sulfuric acid (or oleum) and the compound (A) (in particular wherein $R_0=OH$) is between 0.9 and 5, and/or the molar ratio between the chlorinating agent and the compound (A), (in particular wherein $R_0=OH$) is between 2 and 10.

According to one embodiment, step a) is carried out at a temperature greater than or equal to 90° C., preferably greater than or equal to 100° C., preferentially greater than or equal to 105° C., advantageously greater than or equal to 110° C., even more advantageously greater than or equal to 115° C., and in particular greater than or equal to 120° C.

According to one embodiment, step a) is carried out at a temperature between 105° C. and 130° C., preferably between 105° C. and 125° C., preferentially between 110° C. and 125° C., advantageously between 115° C. and 125° C., and even more preferably between 118° C. and 122° C., and in particular at 120° C.

According to one embodiment, step a) is carried out at a pressure greater than or equal to 7.5 bar abs, preferably greater than or equal to 8 bar abs, more preferably greater than or equal to 9 bar abs, preferentially greater than or equal to 10 bar abs, advantageously greater than or equal to 11 bar abs, even more advantageously greater than or equal to 12 bar abs, preferably greater than or equal to 13 bar abs, for example greater than or equal to 15 bar abs.

Chlorination step a) can be carried out batchwise or semi-continuously.

Step a) can be carried out in a reactor made of a corrosion-resistant material.

Step a) can be carried out in a reactor comprising heating means.

The reactor of step a) can be heated by means of a jacket surrounding the reactor in which a heating fluid can circulate, for example steam, hot water, or a mixture of benzyltoluene and dibenzyltoluene (for example, Jarrytherm BT06).

According to one embodiment, the pressure of the reactor is regulated by a pressure regulating valve. The use of a pressure regulating valve advantageously makes it possible to discharge the gases formed and to maintain the pressure of the reactor at a given pressure.

The pressure adjustment is advantageously independent of the temperature adjustment.

Step a) advantageously makes it possible to provide the compound of formula (I) with a (quasi)-total conversion into sulfamide reagent (A) in a reduced time, preferably in less than 48 hours, advantageously in less than 24 hours, and preferentially in less than 22 hours.

Step a) also makes it possible to reduce the molar ratio between the volatile reagents and the compound (A), and in particular the molar ratio between the chlorinating agent and the compound (A). Indeed, when the pressure is produced at atmospheric pressure in an open medium, the release of gas from the reaction products causes a loss of the volatile reagents during the reaction. Step a) advantageously makes it possible to limit this loss of reagents, and therefore to reduce said molar ratio in the reaction.

The process according to the invention advantageously makes it possible to prepare the compound of formula (IV) in a shorter time, and to reduce the molar ratio between the volatile reagents and the compound (A).

If thionyl chloride is used, step a) results in particular in a release of gas comprising HCl and $SO_2$. The process according to the invention may comprise a step of treating said release of gas, for example by distillation or by means of a membrane, preferably by distillation, for example with a view to exploiting HCl and/or $SO_2$.

The process according to the invention advantageously makes it possible to facilitate the treatment of said release of gas by distillation. Indeed, carrying out step a) under the reaction conditions indicated above (temperature and pressure), advantageously makes it possible to condense HCl at a temperature higher than at atmospheric pressure in the condenser of the column of distillation.

Step b)

The process according to the invention can comprise a step b), subsequent to step a), said step b) comprising reacting the compound of formula (I) obtained in the preceding step, with at least one fluorinating agent, optionally in the presence of at least one organic solvent SO1.

Step b) advantageously allows the fluorination of the compound of formula (I) into a compound of formula (II):

$$R_2—(SO_2)—NH—(SO_2)—F \quad (II)$$

wherein $R_2$ represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$.

Preferably, in formula (II) above, $R_2$ represents F, $CF_3$, $CHF_2$ or $CH_2F$. Particularly preferably, $R_2$ represents F.

According to one embodiment, the fluorinating agent is chosen from the group consisting of HF (preferably anhydrous HF), KF, $AsF_3$, $BiF_3$, $ZnF_2$, $SnF_2$, $PbF_2$, $CuF_2$, and mixtures thereof, the fluorinating agent preferably being HF, and even more preferentially anhydrous HF.

In the context of the invention, the term "anhydrous HF" is intended to mean HF containing less than 500 ppm of water, preferably less than 300 ppm of water, preferably less than 200 ppm of water.

Step b) of the process is preferably carried out in at least one organic solvent SO1. The organic solvent SO1 preferably has a donor number between 1 and 70 and advantageously between 5 and 65. The donor number of a solvent represents the value $-\Delta H$, $\Delta H$ being the enthalpy of the interaction between the solvent and antimony pentachloride (according to the method described in *Journal of Solution Chemistry*, vol. 13, no. 9, 1984). As organic solvent SO1, mention may in particular be made of esters, nitriles, dinitriles, ethers, diethers, amines, phosphines, and mixtures thereof.

Preferably, the organic solvent SO1 is chosen from the group consisting of methyl acetate, ethyl acetate, butyl acetate, acetonitrile, propionitrile, isobutyronitrile, glutaronitrile, dioxane, tetrahydrofuran, triethylamine, tripropylamine, diethylisopropylamine, pyridine, trimethylphosphine, triethylphosphine, diethylisopropylphosphine, and mixtures thereof. In particular, the organic solvent SO1 is dioxane.

Step b) can be carried out at a temperature between 0° C. and the boiling point of the organic solvent SO1 (or of the mixture of organic solvents SO1). Preferably, step b) is carried out at a temperature between 5° C. and the boiling point of the organic solvent SO1 (or of the mixture of organic solvents SO1), preferentially between 20° C. and the boiling point of the organic solvent SO1 (or the mixture of organic solvents SO1).

Step b), preferably with anhydrous hydrofluoric acid, can be carried out at a pressure P, preferably between 0 and 16 bar abs.

This step b) is preferably carried out by dissolving the compound of formula (I) in the organic solvent SO1, or the mixture of organic solvents SO1, prior to the step of reaction with the fluorinating agent, preferably with anhydrous HF.

The weight ratio between the compound of formula (I) and the organic solvent SO1, or the mixture of organic solvents SO1, is preferably between 0.001 and 10, and advantageously between 0.005 and 5.

According to one embodiment, anhydrous HF is introduced into the reaction medium, preferably in gaseous form.

The molar ratio x between the fluorinating agent, preferably the anhydrous HF, and the compound of formula (I) used is preferably between 1 and 10, and advantageously between 1 and 5.

The step of reacting with the fluorinating agent, preferably anhydrous HF, can be carried out in a closed medium or in an open medium, preferably step b) is carried out in an open medium with in particular release of HCl in gas form.

The fluorination reaction typically leads to the formation of HCl, the majority of which can be degassed from the reaction medium (just like the excess HF if the fluorinating agent is HF), for example by stripping with a neutral gas (such as nitrogen, helium or argon).

However, residual HF and/or residual HCl may be dissolved in the reaction medium. In the case of HCl, the amounts are very low because at the working pressure and temperature, the HCl is mainly in gas form.

The composition obtained at the end of step b) can be stored in an HF-resistant container.

The composition obtained in step b) can comprise HF (it is in particular unreacted HF), the compound of formula (II)

mentioned above, the solvent SO1 (such as, for example, dioxane), and optionally HCl, and/or optionally heavy compounds.

The process according to the invention can optionally comprise a step of distilling the composition obtained in step b).

Step c)

The process according to the invention can comprise a step c), subsequent to step b), of reacting the compound of formula (II) obtained in the preceding step (step b)), with a composition comprising at least one alkali or alkaline-earth metal salt This step c) advantageously makes it possible to form a compound of the following formula (III):

$$R_2—(SO_2)—NM-(SO_2)—F \quad (III)$$

wherein $R_2$ is as defined above, and M represents a monovalent or divalent cation of an alkali or alkaline-earth metal.

The alkali or alkaline-earth metal salt may be an alkali or alkaline-earth metal carbonate, or an alkali or alkaline-earth metal hydroxide, or an alkali or alkaline-earth metal chloride, or an alkali or alkaline-earth metal fluoride.

In particular, the alkali or alkaline-earth metal is chosen from: lithium, potassium, sodium, magnesium and calcium, the alkali metal preferably being potassium or lithium, and advantageously potassium.

According to one embodiment, the alkali or alkaline-earth metal salt is chosen from the group consisting of: LiOH, LiOH, $H_2O$, $LiHCO_3$, $Li_2CO_3$, LiCl, LiF, KOH, KOH, $H_2O$, $KHCO_3$, $K_2CO_3$, KCl, $Ca(OH)_2$, $Ca(OH)_2$, $H_2O$, $Ca(HCO_3)_2$, $CaCO_3$, $CaCl_2$, $CaF_2$, $Mg(OH)_2$, $Mg(OH)_2$, $H_2O$, $Mg(HCO_3)_2$, $MgCO_3$, $MgCl_2$, $MgF_2$ and mixtures thereof. Preferably, the alkali or alkaline-earth metal salt is $K_2CO_3$.

When the alkali or alkaline-earth metal salt is a lithium salt, the compound of formula (III) is a compound of formula (IV) mentioned above.

The composition comprising at least one alkali or alkaline-earth metal salt can be an aqueous composition.

The composition comprising at least one alkali or alkaline-earth metal salt can consist of a solid alkali or alkaline-earth metal salt.

Step c) can comprise the addition of the composition obtained in the preceding step to the composition comprising at least one alkali or alkaline-earth metal salt, or the reverse, namely the addition of the composition comprising at least an alkali or alkaline-earth metal salt to the composition obtained in the preceding step.

To determine the amount of alkali or alkaline-earth salt to be introduced, it is typically possible to carry out an analysis of the total acidity of the mixture to be neutralized.

According to one embodiment, step c) is such that:
the molar ratio of the alkali or alkaline-earth salt divided by the number of basicities of said salt relative to the compound of formula (II) is greater than or equal to 1, preferably less than 5, preferably less than 3, preferentially between 1 and 2; and/or
the weight ratio of the alkali or alkaline-earth salt to the weight of water in the aqueous composition is between 0.1 and 2, preferably between 0.2 and 1, preferably between 0.3 and 0.7.

For example, the $K_2CO_3$ salt has a number of basicities equal to 2.

Step c) of the process according to the invention can be carried out at a temperature less than or equal to 40° C.,
preferably less than or equal to 30° C., preferentially less than or equal to 20° C., and in particular less than or equal at 15° C.

According to one embodiment, the process according to the invention comprises an additional step of filtering the composition obtained in step c), resulting in a filtrate F and a cake G.

The compound of formula (III) prepared can be contained in the filtrate F and/or in the cake G.

The filtrate F can be subjected to at least one extraction step with an organic solvent SO2 typically of low solubility in water, in order to extract the compound of formula (III) mentioned above in an organic phase. The extraction step typically results in the separation of an aqueous phase and an organic phase.

In the context of the invention, and unless otherwise indicated, the term "low solubility in water" is intended to mean a solvent of which the solubility in water is less than 5% by weight.

The abovementioned organic solvent SO2 is in particular chosen from the following families: esters, nitriles, ethers, chlorinated solvents and aromatic solvents, and mixtures thereof. Preferably, the organic solvent SO2 is chosen from dichloromethane, ethyl acetate, butyl acetate, tetrahydrofuran and diethyl ether, and mixtures thereof. In particular, the organic solvent SO2 is butyl acetate.

For each extraction, the weight amount of organic solvent used can range between 1/6 and 1 times the weight of the filtrate F. The number of extractions can be between 2 and 10.

Preferably, the organic phase, resulting from the extraction(s), has a weight content of compound of formula (III) ranging from 5% to 40% by weight.

The separated organic phase (obtained at the end of the extraction) can then be concentrated to reach a concentration of compound of formula (III) of between 30% and 60%, preferably between 40% and 50% by weight, it being possible for said concentration to be achieved by any means of evaporation known to those skilled in the art.

The abovementioned cake G can be washed with an organic solvent SO3 chosen from the following families: esters, nitriles, ethers, chlorinated solvents and aromatic solvents, and mixtures thereof. Preferably, the organic solvent SO3 is chosen from dichloromethane, ethyl acetate, butyl acetate, tetrahydrofuran, acetonitrile and diethyl ether, and mixtures thereof. In particular, the organic solvent SO3 is butyl acetate.

The weight amount of organic solvent SO3 used may range between 1 and 10 times the weight of the cake. The total amount of organic solvent SO3 intended for the washing may be used in a single portion or in several portions for the purpose in particular of optimizing the dissolution of the compound of formula (III).

Preferably, the organic phase, resulting from the washing(s) of the cake G, has a weight content of compound of formula (III) ranging from 5% to 20% by weight.

The separated organic phase resulting from the washing(s) of the cake G can then be concentrated to reach a concentration of compound of formula (III) of between 30% and 60%, preferably between 40% and 50% by weight, it being possible for said concentration to be achieved by any means of evaporation known to those skilled in the art.

According to one embodiment, the organic phases resulting from the extraction(s) of the filtrate F and from the washing(s) of the cake G can be combined together, before the concentration step.

Step d)

The process according to the invention can comprise an optional step d), subsequent to step c), of cation exchange between a compound of formula (III) obtained in the preceding step (step c)), and at least one lithium salt.

In particular, the process according to the invention comprises this step d) when the salt obtained in step c) is not a lithium salt.

Step d) is in particular a cation exchange reaction which makes it possible to convert a compound of formula (III) mentioned above into a compound of formula (IV):

$R_2$—$(SO_2)$—$NLi$—$(SO_2)$—F        (IV)

wherein $R_2$ represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$; $R_2$ preferably representing F.

According to one embodiment, the lithium salt is a salt of formula LiX, X representing a fluoride, a chloride, a carbonate, a tetrafluoroborate, a hydroxide, a sulfate, a chlorate, a perchlorate, a nitrile or a nitrate. Preferably, LiX is LiCl.

The abovementioned lithium salt can be dissolved in a polar organic solvent, preferably chosen from the following families: alcohols, nitriles and carbonates. By way of example, mention may in particular be made of methanol, ethanol, acetonitrile, dimethyl carbonate, ethylmethyl carbonate, and mixtures thereof, and preferentially methanol.

The molar ratio of the compound of formula (III) relative to the lithium salt can vary: it can be at least equal to 1 and less than 5. Preferably, the molar ratio of compound of formula (III)/lithium salt is between 1.2 and 2.

The reaction medium can be left to stir for between 1 to 24 hours, and/or at a temperature between for example 0° C. and 50° C.

At the end of the reaction, the reaction medium can be filtered and then optionally be concentrated. The concentration step can optionally be carried out by a thin-film evaporator, by an atomizer, by an evaporator, or by any other device enabling the evaporation of solvent.

Step e)

The process according to the invention can also comprise a step of purifying the compound of formula (IV) mentioned above.

Step d) of purifying the compound of formula (IV) can be carried out by any known conventional method. It may be, for example, an extraction method, a solvent-washing method, a reprecipitation method, a recrystallization method, or a combination thereof.

At the end of step e) mentioned above, the compound of formula (IV) can be in the form of a solid, or of a composition comprising from 1% to 99.9% by weight of compound of formula (IV).

According to a first embodiment, step e) is a step of crystallizing the compound of formula (IV).

Preferably, during step e), the compound of formula (IV) is cold-crystallized, in particular at a temperature less than or equal to 25° C.

Preferably, during step e), the crystallization of the compound of formula (IV) is carried out in an organic solvent ("crystallization solvent") chosen from chlorinated solvents, such as for example dichloromethane, and aromatic solvents, such as for example toluene, and alkanes such as pentane, hexane, cyclohexane or heptane, in particular at a temperature less than or equal to 25° C. Preferably, the compound of formula (IV) crystallized at the end of step (e) is recovered by filtration.

According to a second embodiment, step e) comprises the following steps:
i) optional dissolution of the compound of formula (IV) in an organic solvent S'1,
ii) liquid-liquid extraction of the compound of formula (IV) with deionized water, and recovery of an aqueous solution of said compound of formula (IV);
iii) optional concentration of said aqueous solution of said compound of formula (IV);
iv) liquid-liquid extraction of the compound of formula (IV) from said aqueous solution with at least one organic solvent S'2;
v) concentration of the compound of formula (IV) by evaporation of said organic solvent S'2;
vi) optionally, crystallization of the compound of formula (IV).

It is possible for step e) not to include the abovementioned step i), if the compound of formula (IV) obtained in step d) already comprises an organic solvent (such as for example SO2 and/or SO3).

The abovementioned step ii) comprises in particular the addition of deionized water to the solution of the compound of formula (IV) in the abovementioned organic solvent S'1, to allow the dissolution of said compound of formula (IV), and the extraction of said compound of formula (IV) in water (aqueous phase).

The extraction may be performed via any known extraction means.

According to the invention, step ii) can be repeated at least once, for example three times. In a first extraction, an amount of deionized water corresponding to half of the weight of the initial solution may be added, followed by an amount equal to about a third of the weight of the initial solution during the second extraction, and then an amount equal to about a quarter of the weight of the initial solution during the third extraction.

Preferably, step ii) is such that the weight of deionized water is greater than or equal to one third, preferably greater than or equal to half, of the weight of the initial solution of the compound of formula (III) in the organic solvent S'1 (in the case of a single extraction, or solely for the first extraction if step ii) is repeated at least once).

In the event of multiple extractions (repetition of step ii)), the extracted aqueous phases may be combined together to form a single aqueous solution.

At the end of step ii), an aqueous solution of the compound of formula (IV) is in particular obtained.

According to one embodiment, the weight content of compound of formula (IV) in the aqueous solution is between 5% and 35%, preferably between 10% and 25%, relative to the total weight of the solution.

Preferably, step e) comprises a concentration step iii) between step ii) and step iv), preferably in order to obtain an aqueous solution of the compound of formula (IV) comprising a weight content of compound of formula (IV) between 20% and 80%, in particular between 25% and 80%, preferably between 25% and 70% and advantageously between 30% and 65% relative to the total weight of the solution. The concentration step may be performed with an evaporator under reduced pressure, at a pressure below 50 mbar abs (preferably below 30 mbar abs), and in particular at a temperature between 25° C. and 60° C., preferably between 25° C. and 50° C., preferentially between 25° C. and 40° C., for example at 40° C.

The compound of formula (IV), contained in the aqueous solution obtained at the end of step ii), and of an optional concentration step iii) or of an optional other intermediate step, can then be recovered by extraction with an organic solvent S'2, said solvent S'2 (step iv)). Step iv) results in particular, after extraction, in an organic phase, saturated with water, containing the compound of formula (IV) (it is a solution of compound of formula (IV) in the organic solvent S'2, said solution being saturated with water).

Step iv) advantageously allows the production of an aqueous phase and an organic phase, which are separate.

Preferably, the organic solvent S'2 is chosen from the group consisting of esters, nitriles, ethers, chlorinated solvents and aromatic solvents, and mixtures thereof. Preferably, the solvent S'2 is chosen from ethers and esters, and mixtures thereof. For example, mention may be made of diethyl carbonate, methyl t-butyl ether, cyclopentyl methyl ether, ethyl acetate, propyl acetate, butyl acetate, dichloromethane, tetrahydrofuran, acetonitrile and diethyl ether, and mixtures thereof. Preferably, the solvent S'2 is chosen from methyl t-butyl ether, cyclopentyl methyl ether, ethyl acetate, propyl acetate and butyl acetate, and mixtures thereof. In particular, the organic solvent S'2 is butyl acetate.

The extraction step iv) is repeated at least once, preferably from one to ten times and in particular four times. The organic phases may then be combined into a single phase before step v). For each extraction, the weight amount of organic solvent S'2 used may range between 1/6 and 1 times the weight of the aqueous phase. Preferably, the organic solvent S'2/water weight ratio, during an extraction of step iv), ranges from 1/6 to 1/1, the number of extractions ranging in particular from 2 to 10.

Preferably, during the extraction step iv), the organic solvent S'2 is added to the aqueous solution resulting from step ii) (and from the optional step iii)).

Step e) according to this embodiment can comprise a preconcentration step between step iv) and step v), preferably to obtain a solution of the compound of formula (IV) in the organic solvent S'2 comprising a weight content of compound of formula (IV) of between 20% and 60%, and preferably between 30% and 50% by weight relative to the total weight of the solution. The pre-concentration step can be carried out at a temperature ranging from 25° C. to 60° C., preferably from 25° C. to 45° C., optionally under reduced pressure, for example at a pressure less than 50 mbar abs, in particular at a pressure less than 30 mbar abs. The pre-concentration step is preferably carried out by an evaporator under reduced pressure, in particular at 40° C. and at a pressure less than 30 mbar abs.

According to the invention, the concentration step v) may be performed at a pressure of between $10^{-2}$ mbar abs and 5 mbar abs, preferably between $5 \times 10^{-2}$ mbar abs and 2 mbar abs, preferentially between $5 \times 10^{-1}$ and 2 mbar abs, even more preferentially between 0.1 and 1 mbar abs and in particular between 0.4 and 0.6 mbar abs. In particular, step c) is performed at 0.5 mbar abs or at 0.1 mbar.

According to one embodiment, step v) is carried out at a temperature between 30° C. and 95° C., preferably between 30° C. and 90° C., preferentially between 40° C. and 85° C., and in particular between 50° C. and 70° C.

According to one embodiment, step v) is performed with a residence time of less than or equal to 15 minutes, preferentially less than 10 minutes, preferably less than or equal to 5 minutes and advantageously less than or equal to 3 minutes.

In the context of the invention, and unless otherwise mentioned, the term "residence time" is intended to mean the time which elapses between the entry of the solution of the compound of formula (III) (in particular obtained at the end of the abovementioned step iv)) into the evaporator and the exit of the first drop of the solution.

According to one preferred embodiment, the temperature of the condenser of the thin-film short-path evaporator is between −55° C. and 10° C., preferably between −50° C. and 5° C., more preferentially between −45° C. and −10° C., and advantageously between −40° C. and −15° C.

The abovementioned thin-film short-path evaporators are also known under the name "wiped-film short-path" (WFSP). They are typically referred to as such since the vapors generated during the evaporation cover a short path (travel a short distance) before being condensed in the condenser.

Among the thin-film short-path evaporators, mention may be made especially of the evaporators sold by the companies Buss SMS Ganzler ex Luwa AG, UIC GmbH or VTA Process.

Typically, the thin-film short-path evaporators may comprise a condenser for the solvent vapors, placed inside the machine itself (in particular at the center of the machine), unlike other types of thin-film evaporator (which are not short-path evaporators) in which the condenser is outside the machine.

In this type of machine, the formation of a thin film, of product to be distilled, on the hot inner wall of the evaporator may typically be ensured by continuous spreading over the evaporation surface with the aid of mechanical means specified below.

The evaporator may especially be equipped, at its center, with an axial rotor on which are mounted the mechanical means that allow the formation of the film on the wall. They may be rotors equipped with fixed vanes, lobed rotors with three or four vanes made of flexible or rigid materials, distributed over the entire height of the rotor, or rotors equipped with mobile vanes, paddles, brushes, doctor blades or guided scrapers. In this case, the rotor may be constituted by a succession of pivot-articulated paddles mounted on a shaft or axle by means of radial supports. Other rotors may be equipped with mobile rollers mounted on secondary axles and said rollers are held tight against the wall by centrifugation. The spin speed of the rotor, which depends on the size of the machine, may be readily determined by those skilled in the art. The various spindles may be made of various materials: metallic, for example steel, steel alloy (stainless steel), aluminum, or polymeric, for example polytetrafluoroethylene PTFE, or glass materials (enamel); metallic materials coated with polymeric materials.

Process

The process according to the present invention is particularly advantageous for producing the following compounds of formula (IV): $LiN(SO_2F)_2$, $LiNSO_2CF_3SO_2F$, $LiNSO_2C_2F_5SO_2F$, $Li NSO_2CF_2OCF_3SO_2F$, $LiNSO_2C_3HF_6SO_2F$, $LiNSO_2C_4F_9SO_2F$, $LiNSO_2C_5F_{11}SO_2F$, $LiNSO_2C_6F_{13}SO_2F$, $LiNSO_2C_7F_{15}SO_2F$, $LiNSO_2C_8F_{17}SO_2F$ and $LiNSO_2C_9F_{19}SO_2F$.

Preferably, the process according to the invention is a process for preparing $LiN(SO_2F)_2$ (LiFSI).

In the context of the invention, the terms "lithium bis (fluorosulfonyl)imide salt", "lithium bis(sulfonyl)imide", "LiFSI", "$LiN(SO_2F)_2$", "lithium bis(sulfonyl)imide" and "lithium bis(fluorosulfonyl)imide" are used equivalently.

In the context of the invention, the term "between x and y" or "ranging from x to y" means a range in which the limits x and y are included. For example, the temperature "between −20 and 80° C." especially includes the values −20° C. and 80° C.

All the embodiments described above can be combined with one another. In particular, each embodiment of any step of the process of the invention may be combined with another particular embodiment.

The present invention is illustrated by the example which follows, to which it is not, however, limited.

EXAMPLES

Example 1 (Comparative): Reaction at Atmospheric Pressure

Sulfamic acid (1 eq, 1.24 mol, 120 g) and 95% sulfuric acid (1 eq, 1.24 mol, 127.5 g) are charged to a one-liter glass reactor fitted with stirrer. Thionyl chloride (4 eq, 4.9 mol, 583 g) is gradually added to the reactor using a dropping funnel. The temperature of the reaction medium is maintained at 35° C. for 2 hours and then is gradually increased to 75° C. The reaction is maintained at a temperature of 75° C. for 64 hours in order to obtain complete conversion to sulfamic acid. A condenser operating with cold water is placed on the vent line of the reactor so as to condense the vaporized thionyl chloride and to reflux it into the reaction medium. The gases generated by the reaction (HCl and $SO_2$) and not condensed by the condenser are directed to a bubbler containing water, where they are absorbed.

321.5 g of liquid containing bis(chlorosulfonyl)imide and residual thionyl chloride are obtained.

Example 2: Reaction at 8 Bar Absolute

Sulfamic acid (1 eq, 0.41 mol, 40 g) and thionyl chloride (3.25 eq, 1.34 mol, 159.3 g) are charged to a glass reactor. 20% oleum (1 eq, 0.41 mol, 38.9 g) is gradually added to the reactor. The reaction medium is stirred and is heated until a temperature of 120° C. is obtained. The pressure of the reactor is regulated at 8 bar absolute by means of an overflow placed on the discharge of the reactor vent. Downstream of the overflow, this vent is directed to a bubbler containing 1 kg of water allowing the gases to be absorbed. The reaction time is 20 hours to obtain complete conversion to sulfamic acid. The bis(chlorosulfonyl)imide obtained in the end has a light yellow appearance. At the end of the reaction, 136.4 g of liquid containing the bis(chlorosulfonyl)imide, residual thionyl chloride and solubilized $SO_2$ are recovered.

Example 3 (Comparative): Reaction at Atmospheric Pressure

Sulfamic acid (1 eq, 1.24 mol, 120 g) and 95% sulfuric acid (1 eq, 1.24 mol, 127.5 g) are charged to a one-liter glass reactor fitted with stirrer. Thionyl chloride (4 eq, 4.9 mol, 583 g) is gradually added to the reactor using a dropping funnel. The temperature of the reaction medium is gradually increased to 90° C. The reaction is carried out at atmospheric pressure. Total conversion to sulfamic acid is obtained after 52 hours. A condenser operating with cold water is placed on the vent line of the reactor so as to condense the vaporized thionyl chloride and to reflux it into the reaction medium. The gases generated by the reaction (HCl and $SO_2$) and those not condensed by the condenser are directed to a bubbler containing water, where they are absorbed.

319.5 g of liquid containing bis(chlorosulfonyl)imide and residual thionyl chloride are obtained.

Example 4: Reaction at 8 Bar Absolute

Sulfamic acid (1 eq, 1.24 mol, 120 g) and 95% sulfuric acid (1 eq, 1.24 mol, 127.5 g) are charged to a one-liter glass reactor fitted with stirrer. Thionyl chloride (4 eq, 4.9 mol, 583 g) is gradually added to the reactor using a dropping funnel. The temperature of the reaction medium is gradually increased to 90° C. The pressure of the reactor is regulated at 8 bar absolute by means of an overflow placed on the discharge of the reactor vent. Downstream of the overflow, this vent is directed to a bubbler containing water allowing the gases to be absorbed.

Total conversion to sulfamic acid is achieved in less than 52 hours. 323 g of liquid containing bis(chlorosulfonyl)imide and residual thionyl chloride are obtained.

Example 5: Reaction at 8 Bar Absolute

Sulfamic acid (1 eq, 1.24 mol, 120 g) and 95% sulfuric acid (1 eq, 1.24 mol, 127.5 g) are charged to a one-liter glass reactor fitted with stirrer. Thionyl chloride (3.5 eq, 4.9 mol, 583 g) is gradually added to the reactor using a dropping funnel. The temperature of the reaction medium is gradually increased to 90° C. The pressure of the reactor is regulated at 8 bar absolute by means of an overflow placed on the discharge of the reactor vent. Downstream of the overflow, this vent is directed to a bubbler containing water allowing the gases to be absorbed.

Total conversion to sulfamic acid is achieved in less than 52 hours. 320.5 g of liquid containing bis(chlorosulfonyl)imide and residual thionyl chloride are obtained.

The comparison of examples 3 and 4 shows that carrying out the chlorination reaction under a pressure of 8 bar (example 4) advantageously makes it possible to obtain total conversion to sulfamic acid in a reduced time compared to carrying out said reaction at atmospheric pressure (example 3).

In addition, the chlorination reaction carried out under a pressure of 8 bar advantageously makes it possible to reduce the time to obtain total conversion to sulfamic acid while at the same time reducing the molar amount of thionyl chloride (example 5) compared to the reaction under atmospheric pressure (example 3).

Example 6: Preparation of LiFSI

LiFSI was prepared from each of the bis(chlorosulfonyl)imides obtained in examples 1 to 5, according to the procedure described in example 3 of WO 2014/080120.

The invention claimed is:

1. A process for preparing a compound of the following formula (IV)

$$R_2—(SO_2)—NLi—(SO_2)—F \qquad (IV)$$

wherein $R_2$ represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$;

said process comprising a step a) of reacting a sulfamide of the following formula (A):

$$R_0—(SO_2)—NH_2 \qquad (A)$$

wherein $R_0$ represents one of the following radicals: OH, Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$;

with at least one sulfur-containing acid and at least one chlorinating agent, said step a) being carried out:
at a temperature between 90° C. and 130° C., and
at a pressure of at least 8 bar abs, wherein the reaction of step a) produces a chlorinated product of the following formula (I):

$$R_1-(SO_2)-NH-(SO_2)-Cl \qquad (I)$$

wherein $R_1$ represents one of the following radicals: Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$.

2. The process as claimed in claim 1, wherein the compound (A) is that wherein $R_0$ represents OH.

3. The process as claimed in claim 1, wherein the sulfur-containing agent is chosen from the group consisting of chlorosulfonic acid ($ClSO_3H$), sulfuric acid, oleum, and mixtures thereof.

4. The process as claimed in claim 1, wherein the chlorinating agent is chosen from the group consisting of thionyl chloride ($SOCl_2$), oxalyl chloride ($COCl_2$), phosphorus pentachloride ($PCl_5$), phosphonyl trichloride ($PCl_3$), phosphoryl trichloride ($POCl_3$), and mixtures thereof.

5. The process as claimed in claim 1, wherein:
the molar ratio between the sulfur-containing acid and the compound (A) is between 0.7 and 5; and/or
the molar ratio between the chlorinating agent and the compound (A) is between 2 and 10.

6. The process as claimed in claim 1, wherein step a) is carried out at a temperature between 105° C. and 130° C.

7. The process as claimed in claim 1, wherein step a) is carried out at a pressure greater than or equal to 8.5 bar abs.

8. The process as claimed in claim 1, comprising a step b), subsequent to step a), said step b) comprising reacting the chlorinated compound of formula (I) obtained in the preceding step:

$$R_1-(SO_2)-NH-(SO_2)-Cl \qquad (I)$$

wherein $R_1$ represents one of the following radicals: Cl, F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$;

with at least one fluorinating agent, optionally in the presence of at least one organic solvent SO1.

9. The process as claimed in claim 8, wherein the fluorinating agent is chosen from the group consisting of HF, KF, $AsF_3$, $BiF_3$, $ZnF_2$, $SnF_2$, $PbF_2$, $CuF_2$, and mixtures thereof.

10. The process as claimed in claim 8, comprising a step c), subsequent to step b), of reacting the compound of formula (II) obtained in the preceding step:

$$R_2-(SO_2)-NH-(SO_2)-F \qquad (II)$$

wherein $R_2$ represents one of the following radicals: F, $CF_3$, $CHF_2$, $CH_2F$, $C_2HF_4$, $C_2H_2F_3$, $C_2H_3F_2$, $C_2F_5$, $C_3F_7$, $C_3H_4F_3$, $C_3HF_6$, $C_4F_9$, $C_4H_2F_7$, $C_4H_4F_5$, $C_5F_{11}$, $C_6F_{13}$, $C_7F_{15}$, $C_8F_{17}$ or $C_9F_{19}$;
with a composition comprising at least one alkali or alkaline-earth metal salt.

11. The process as claimed in claim 10, wherein the alkali or alkaline-earth metal salt is an alkali or alkaline-earth metal carbonate, or an alkali or alkaline-earth metal hydroxide, or an alkali or alkaline-earth metal chloride, or an alkali or alkaline-earth metal fluoride.

12. The process as claimed in claim 10, comprising a step d), subsequent to step c), of cation exchange between a compound of formula (III) obtained in the preceding step:

$$R_2-(SO_2)-NM-(SO_2)-F \qquad (III)$$

wherein R2 is as defined in claim 1, and M represents a monovalent or divalent cation of an alkali or alkaline-earth metal;
and at least one lithium salt.

13. The process as claimed in claim 1, wherein $R_2$ represents F.

14. The process as claimed in claim 1, wherein the sulfur-containing agent is sulfuric acid or oleum.

15. The process as claimed in claim 1, wherein the sulfur-containing agent is sulfuric acid.

16. The process as claimed in claim 1, wherein the chlorinating agent is thionyl chloride.

* * * * *